United States Patent
Bhatt et al.

(10) Patent No.: US 10,800,716 B2
(45) Date of Patent: Oct. 13, 2020

(54) PROCESS FOR PRODUCING OLEFINS FROM SYNGAS

(71) Applicant: RELIANCE INDUSTRIES LIMITED, Mumbai (IN)

(72) Inventors: Ujjval Bhadrashankar Bhatt, Mumbai (IN); Pravin Badrinarayan Kalantri, Mumbai (IN); Jayant Vishnu Kelkar, Mumbai (IN); Shridhar Bhalchandra Dingankar, Thane (IN)

(73) Assignee: RELIANCE INDUSTRIES LIMITED, Mumbai (IN)

( * ) Notice: Subject to any disclaimer, the term of this patent is extended or adjusted under 35 U.S.C. 154(b) by 0 days.

(21) Appl. No.: 16/314,177

(22) PCT Filed: Jun. 28, 2017

(86) PCT No.: PCT/IB2017/053865
§ 371 (c)(1),
(2) Date: Dec. 28, 2018

(87) PCT Pub. No.: WO2018/002838
PCT Pub. Date: Jan. 4, 2018

(65) Prior Publication Data
US 2019/0284108 A1 Sep. 19, 2019

(30) Foreign Application Priority Data
Jun. 29, 2016 (IN) .............................. 201621022322

(51) Int. Cl.
*C07C 1/24* (2006.01)
*C07C 41/01* (2006.01)
(Continued)

(52) U.S. Cl.
CPC .................. *C07C 1/24* (2013.01); *C01B 3/34* (2013.01); *C07C 1/20* (2013.01); *C07C 41/01* (2013.01);
(Continued)

(58) Field of Classification Search
CPC ... C07C 1/24; C07C 41/01; C10J 3/72; C01B 3/34
See application file for complete search history.

(56) References Cited

U.S. PATENT DOCUMENTS

2013/0197288 A1* 8/2013 Schafer ................ C07C 1/0425
585/324

FOREIGN PATENT DOCUMENTS

WO 2008/101403 A1 8/2008
WO 2009/130292 A2 10/2009

OTHER PUBLICATIONS

Wang et al. (Carbon dioxide reforming of methane to produce synthesis gas over metal-supported catalysts: State of art, 1996, Energy and Fuels, vol. 10, pp. 896-904) (Year: 1996).*
(Continued)

*Primary Examiner* — Youngsul Jeong
(74) *Attorney, Agent, or Firm* — McCarter & English, LLP

(57) ABSTRACT

The present disclosure relates to an improved process for producing olefins from syngas. Raw material is treated to produce syngas comprising $H_2$, CO and $CO_2$. The ratio of $H_2$ and CO in the syngas is 1:1. The syngas is contacted with at least one first catalyst to produce an intermediate stream comprising dimethyl ether (DME), and unconverted $CO_2$, $H_2$ and CO. The unconverted $H_2$ and CO is recycled to a first catalyst section and a portion of the separated $CO_2$ is recycled for producing the syngas. The remaining intermediate stream is contacted with at least one second catalyst to
(Continued)

produce a second stream comprising olefins, $H_2O$, methane, ethane, and propane. $H_2O$, methane, ethane, and propane are separated to obtain the olefins. The separated methane, ethane, and propane are further recycled for producing the syngas. The CAPEX and OPEX of the improved process are reduced.

3 Claims, 2 Drawing Sheets

(51) Int. Cl.
*C07C 1/20* (2006.01)
*C10J 3/72* (2006.01)
*C01B 3/34* (2006.01)

(52) U.S. Cl.
CPC .......... *C10J 3/72* (2013.01); *C01B 2203/0205* (2013.01); *C01B 2203/06* (2013.01); *C01B 2203/148* (2013.01); *C07C 2529/40* (2013.01); *C10J 2300/1656* (2013.01); *Y02P 20/584* (2015.11); *Y02P 30/42* (2015.11)

(56) References Cited

OTHER PUBLICATIONS

International Search Report and Written Opinion of the International Searching Authority, dated Sep. 21, 2017, issued in connection with International Application No. PCT/IB2017/053865 (8 pages).

\* cited by examiner

PROCESS FOR PRODUCING OLEFINS FROM SYNGAS

RELATED APPLICATIONS

This application is a U.S. National Phase Application under 35 U.S.C. 371 of International Application No. PCT/IB2017/053865 filed on Jun. 28, 2017, which was published on Jan. 4, 2018 under International Publication Number WO 2018/002838 A1, and which claims the benefit of Indian Patent Application No. 201621022322 filed on Jun. 29, 2016. The disclosures of these applications are incorporated herein by reference in their entireties.

FIELD

The present disclosure relates to an improved process for producing olefins from syngas.

BACKGROUND

Syngas is generally a mixture of hydrogen ($H_2$), carbon monoxide (CO). However, due to process inefficiency, carbon dioxide ($CO_2$) is also produced along with syngas. Syngas can be used in a variety of applications such as production of methanol, production of dimethyl ether (DME), production of olefins, production of ammonia, production of urea, heating, generation of steam and generation of power. Syngas can be produced by utilizing methane or natural gas, liquid fuels or solid fuels such as coal, petcoke, biomass, solid wastes, and the like.

The following reactions or processes illustrate the production of syngas:

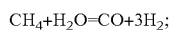      i. steam reforming: $CH_4 + H_2O = CO + 3H_2$;

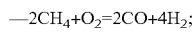      ii. partial oxidation: $-2CH_4 + O_2 = 2CO + 4H_2$;

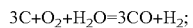      iii. coal gasification: $3C + O_2 + H_2O = 3CO + H_2$;

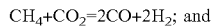      iv. dry reforming: $CH_4 + CO_2 = 2CO + 2H_2$; and

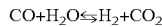      v. water-gas shift reaction: $CO + H_2O \leftrightarrows H_2 + CO_2$ The ratio of $H_2$ and CO in syngas varies depending upon the raw materials used and the process or reaction conditions used for producing syngas.

Figure 1:
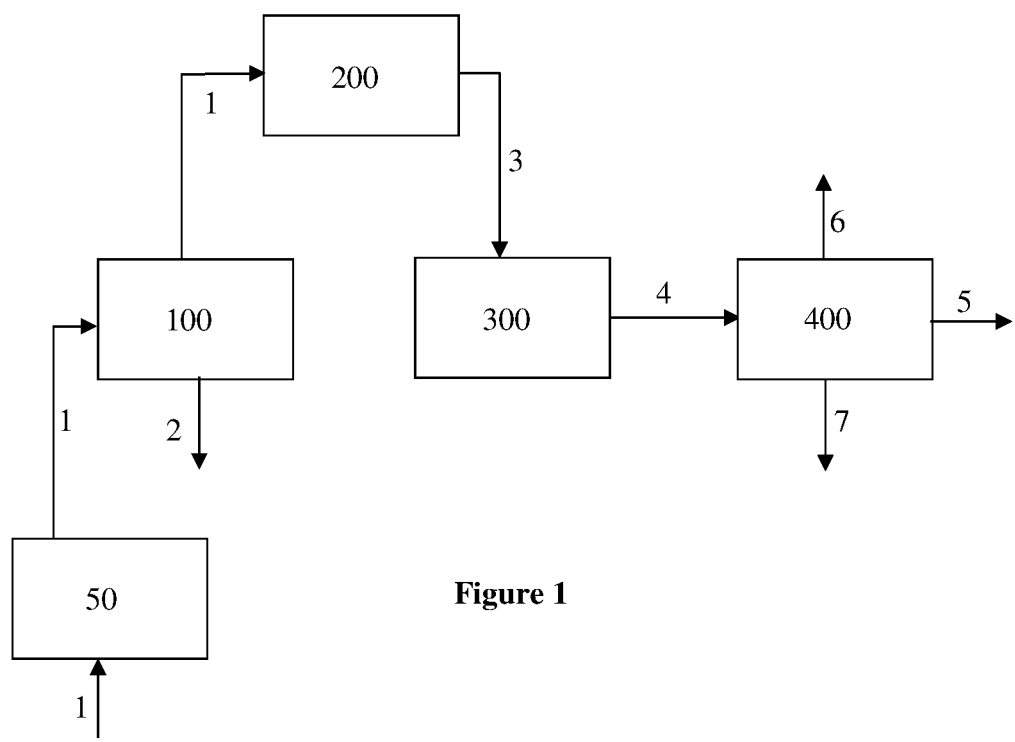

FIG. 1 depicts a flow-path, illustrating a conventional process for producing olefins from syngas. Syngas (1) is first converted into methanol (3), and then methanol is converted into olefins. For the production of methanol, syngas (1) comprising 2:1 ratio of $H_2$ and CO is used. Syngas (1) is introduced into a water-gas shift reactor/section (50), wherein the proportion of $H_2$ can be increased. Since the amount of $CO_2$ (2) produced during the production of syngas (1) is significant, in order to meet the requirement of 2:1 ratio of $H_2$ and CO, there is a need to separate $CO_2$ (2) from the syngas (1). Therefore, the syngas (1) from the water-gas shift reactor/section (50) is introduced into a separator (100). After the separation of $CO_2$ (2), the syngas (1), which is deficient of $CO_2$, is introduced into a reactor (200) for producing methanol (3). The reaction for producing methanol (3) is depicted herein below:

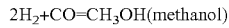 $2H_2 + CO = CH_3OH$ (methanol)

Methanol (3) is then introduced into a reactor (300), wherein methanol (3) is dehydrogenated to produce a stream (4) comprising olefins (5), unconverted DME (6) and $H_2O$ (7) in the reactor (300). The stream (4) is further introduced into a separator (400) for separating unconverted DME (6) and $H_2O$ (7) from stream (4) to obtain olefins (5). The separated $H_2O$ (7) and the unconverted DME (6) can be further utilized for producing syngas (1) and olefins (5) respectively.

Moreover, the amount of $CO_2$ produced during this process is significant because:

$CO_2$ is present in syngas; and syngas with low $H_2$ and high CO needs to be converted to syngas comprising 2:1 ratio of $H_2$ and CO. This can be done by water-gas shift, wherein CO is reacted with water to generate $H_2$, and $CO_2$ as a by-product.

A separate process equipment is required for separating carbon dioxide from syngas. Also, the amount of energy required to separate carbon dioxide from syngas is more due to the presence of a significant amount $CO_2$ in syngas. This increases the capital expenditure (CAPEX) and operational expenditure (OPEX) of the conventional process for producing olefins.

Moreover, syngas comprising 2:1 ratio of $H_2$ and CO results in the conversion of syngas to methanol at a particular temperature (in the range of 300° C. to 400° C.) and pressure (in the range of 60 bar to 90 bar) conditions, thereby requiring a reactor for producing methanol. Also, different process equipment like heaters and compressors are required for achieving the specific temperature and pressure conditions in the reactor. This results in further increase in the capital expenditure (CAPEX) and operational expenditure (OPEX) of the conventional process for producing olefins.

Therefore, there is a need for a process for producing olefins with reduced generation and possible utilization of $CO_2$. Further, there is a need for a process for producing olefins with reduced CAPEX and OPEX of the process, which minimizes the multiple reactors operating at different temperature and pressure conditions.

Objects

Some of the objects of the present disclosure, which at least one embodiment herein satisfies, are as follows.

An object of the present disclosure is to provide a process with reduced generation of $CO_2$.

Yet another object of the present disclosure is to provide a process which can inherently consume less energy along with elimination of equipment/process conditions for the intermediate process.

Yet another object of the present disclosure is to separate $CO_2$ post the DME production to minimize the energy need for separation.

Still another object of the present disclosure is to efficiently utilize separated streams like $CO_2$, methane, ethane, and propane to produce syngas.

Another object of the present disclosure is to provide a process for producing olefins with reduced CAPEX and OPEX of the process.

Other objects and advantages of the present disclosure will be more apparent from the following description, which is not intended to limit the scope of the present disclosure.

SUMMARY

The present disclosure envisages a process for producing olefins from syngas comprising $H_2$, CO and $CO_2$. Typically, the ratio of $H_2$ and CO of the syngas (first stream), is 1:1. The syngas is contacted with at least one first catalyst, at a pre-determined temperature and at a pre-determined pressure, to produce an intermediate stream comprising dimethyl ether (DME) and unconverted $CO_2$, $H_2$ and CO. The unconverted $H_2$ and CO is recycled to a first catalyst section, and a portion of the separated $CO_2$ is recycled for producing the syngas. The remaining intermediate stream is further contacted with a second catalyst, at a pre-determined temperature and at a pre-determined pressure, to produce a second stream comprising olefins, $H_2O$, methane, ethane, and propane. $H_2O$, methane, ethane, and propane are separated from the second stream to obtain olefins. The separated $CO_2$, $H_2O$, methane, ethane, and propane are further recycled for producing the syngas.

The olefins can be at least one of ethylene and propylene.

The process of the present disclosure reduces the generation of $CO_2$.

The process of the present disclosure also reduces the CAPEX and the OPEX of the entire process.

BRIEF DESCRIPTION OF ACCOMPANYING DRAWING

Figure 2:
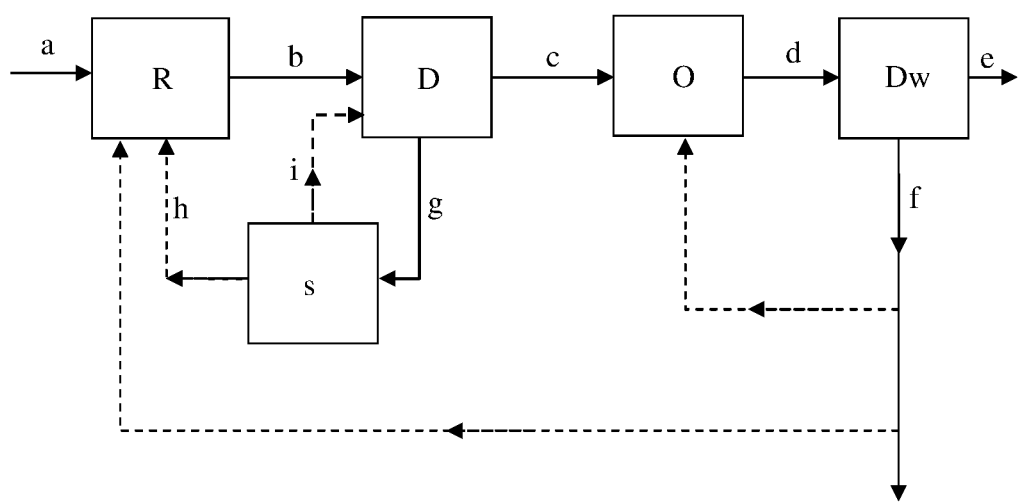

A process for producing olefins from a gaseous mixture will now be described with the help of the accompanying drawing, in which:

FIG. 1 depicts a flow-path, illustrating a conventional process for producing olefins; and FIG. 2 depicts a flow-path for producing olefins in accordance with the present disclosure.

Table 1 provides a list the elements of the process of the present disclosure and their respective reference letters:

TABLE 1

| Elements | Reference letters |
|---|---|
| Raw material | (a) |
| Gasifier/reformer | (R) |
| First stream (Syngas) | (b) |
| DME (dimethyl ether) reactor | (D) |
| Intermediate stream | (c) |
| Separator | (s) |
| Separated portion | (g) |
| Separated $CO_2$ | (h) |
| Separated $H_2$ and CO | (i) |
| Reactor | (O) |
| Second stream | (d) |
| Fractionation column or divided wall column | (Dw) |
| Olefins | (e) |
| Separated stream | (f) |

DETAILED DESCRIPTION

2:1 ratio of $H_2$ and CO in syngas leads to generation of an excess amount of $CO_2$, and an excess use of $H_2O$. Moreover, for economic viability of the methanol production process, $CO_2$ should be minimum or nil in the feed. Therefore, it is necessary to completely separate or remove $CO_2$. Separation of $CO_2$ requires bigger separation units, which consume a significant amount of energy, and $H_2O$ passes through all the equipment due to which the size of the equipment increases, thereby increasing the CAPEX and OPEX of the entire process.

The present disclosure, therefore, provides an improved process for producing olefins with reduced generation of $CO_2$ and with reduced CAPEX and OPEX of the entire process.

The process for producing olefins is illustrated with reference to FIG. 2. Raw material (a) is treated in a gasifier/reformer (R), typically at a temperature in the range of 300° C. to 1000° C. and at a pressure in the range of 1 kg/cm² to 80 kg/cm², to produce a first stream (b), i.e., syngas comprising $H_2$, CO and $CO_2$, wherein the ratio of $H_2$ and CO in the syngas is 1:1.

The raw material (a) can be at least one of coal, petcoke, biomass, natural gas or liquid fuels.

In the process of the present disclosure, the amount of $CO_2$ produced during the production of syngas is significantly less. Additionally, the one-step dimethyl ether (DME) process of the present disclosure can handle a significant amount of $CO_2$ in the feed, as compared to the conventional methanol process. Therefore, separation of $CO_2$ from syngas (b) in a separate process equipment is obviated at this stage.

The first stream, i.e., syngas, (b) is directly introduced into a DME reactor (D), wherein syngas (b) is contacted with a first catalyst in the DME reactor (D), typically at a temperature in the range of 100° C. to 400° C. and at a pressure in the range of 1 kg/cm² to 60 kg/cm², to produce an intermediate stream (c) comprising dimethyl ether (DME) and unconverted $CO_2$, $H_2$ and CO. $CO_2$, and the unconverted $H_2$ and CO can be separated from the intermediate stream (c) with less energy requirement as $CO_2$ concentration is relatively higher. Due to the reduced criticality of the process equipment used for separating $CO_2$, a simpler separation process equipment can be used. The separated portion (g) is introduced into a separator (s) for separating $CO_2$ (h), $H_2$ and CO (i). The separated $CO_2$ (h) can be recycled for producing syngas, and the separated $H_2$ and CO (i) can be recycled to the DME reactor (D).

The first catalyst includes, but is not limited to, copper oxide, chromium oxide, zinc oxide and aluminium oxide.

One-step DME process requires $H_2$:CO ratio of 1:1, which leads to smaller water-gas shift reaction and lower water consumption and $CO_2$ generation. As the portion of $CO_2$ in the syngas is lower, the one-step DME process can handle syngas without removing $CO_2$.

The intermediate stream (c) is introduced into a reactor (O) and contacted with a second catalyst in the reactor (O), typically at a temperature in the range of 200° C. to 600° C. and at a pressure in the range of 0.5 kg/cm² to 10 kg/cm², to produce a second stream (d) comprising olefins, $H_2O$, unreacted DME, methane, ethane, and propane.

The second catalyst includes, but is not limited to, molecular sieve catalysts.

In accordance with one embodiment of the present disclosure, the second catalyst is at least one selected from the group consisting of salts, aluminophosphate (ALPO) molecular sieves, and silicoaluminophosphate (SAPO) molecular sieves, as well as substituted forms thereof.

In accordance with another embodiment of the present disclosure, the second catalyst is ZSM-5.

The second stream (d) is introduced into a fractionation column or a divided wall column (Dw) for separating $H_2O$, unreacted DME, methane, ethane, and propane from the second stream (d) to obtain olefins (e) and a separated stream (f).

The separated $CO_2$, $H_2O$, methane, ethane, and propane can be recycled into the reformer for producing syngas by at least one of dry reforming, bi-reforming, or tri-reforming, wherein syngas with higher $H_2$ and CO is produced as compared to gasification.

Dry reforming of natural gas is depicted herein below:

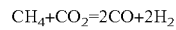

Moreover, the amount of raw materials required for producing syngas (b) is reduced, since the separated methane, ethane and propane are utilized for producing syngas, which is significantly rich in $H_2$. Also, the separated unreacted DME can be recycled into the DME reactor (D) for producing the intermediate stream (c).

In accordance with one embodiment of the present disclosure, a portion of the separated $CO_2$ is recycled into the reformer and a remaining portion of the separated $CO_2$ is vented out to the atmosphere.

Moreover, the amount of $H_2O$ generated in the reactor (O) can be approximately 50% less as compared to that generated conventionally during the production of olefins from syngas comprising 2:1 ratio of $H_2$ and CO.

In accordance with one embodiment of the present disclosure, the second stream (d) can be introduced into a de-methanation column (not shown in FIG. 2) for separating methane contained therein.

As described herein above, syngas (b) comprising 1:1 ratio of $H_2$ and CO is utilized for producing olefins (e). Due to 1:1 ratio of $H_2$ and CO:

the amount of raw materials required for producing syngas (b) is reduced, because the separated $CO_2$, methane, ethane and propane are utilized for producing syngas which is significantly rich in $H_2$;

the amount of $CO_2$ produced during the production of syngas (b) and water-gas shift reaction is significantly less, and one step DME process can accommodate $CO_2$ in the feed, which leads to smaller and less severe $CO_2$ separating process equipment post DME;

the intermediate step of methanol production, of conventional processes, is obviated, thereby eliminating the use of a reactor for producing methanol;

efficient separation of the streams by the use of a divided wall column leads to an even more reduction in energy need for separation and saving in the CAPEX of the entire process; and the amount of water being circulated from gasification to olefins is significantly reduced, which leads to reduced volume of many intermediate sections.

Due to the above mentioned factors, the CAPEX is significantly reduced and the OPEX is reduced upto 30%, as compared to that of the conventional process.

Technical Advances and Economical Significance

The present disclosure described herein above has several technical advantages including, but not limited to, the realization of an improved process that:

reduces generation of $CO_2$ during the process for producing olefins;

utilizes $CO_2$ in olefins production;

reduces energy needs for separating products;

reduces energy needs for separating $CO_2$;

reduces circulation of $H_2O$ in the process with lower water-gas shift reaction; and reduces CAPEX and OPEX for producing olefins.

The disclosure has been described with reference to the accompanying embodiments which do not limit the scope and ambit of the disclosure. The description provided is purely by way of example and illustration.

The embodiments herein and the various features and advantageous details thereof are explained with reference to the non-limiting embodiments in the following description. Descriptions of well-known components and processing techniques are omitted so as to not unnecessarily obscure the embodiments herein.

The foregoing description of the specific embodiments so fully revealed the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

We claim:

1. A process for producing olefins from syngas, said process comprising the following steps:

(a) treating raw material, at a temperature in a range of 300° C. to 1000° C. and at a pressure in a range of 1 $kg/cm^2$ to 80 $kg/cm^2$, to produce a first stream, containing syngas comprising $H_2$, CO and $CO_2$, wherein a volume ratio of $H_2$ and CO in said syngas is 1:1, wherein said raw material is at least one selected from the group consisting of coal, petcoke, biomass, natural gas and liquid fuels;

(b) contacting said syngas with at least one first catalyst, at a temperature in a range of 100° C. to 400° C. and at a pressure in a range of 1 $kg/cm^2$ to 60 $kg/cm^2$, to produce an intermediate stream comprising dimethyl ether (DME), unconverted $CO_2$, $H_2$, and CO, wherein said at least one first catalyst is selected from the group consisting of chromium oxide, zinc oxide and aluminium oxide, wherein said intermediate stream is devoid of methanol;

(c) separating a portion of $CO_2$, $H_2$, and CO from said intermediate stream and recycling the separated portion of $CO_2$ to step (a) for producing said syngas and recycling the separated portion of $H_2$, and CO to step (b) for producing said DME;

(d) contacting said intermediate stream with at least one second catalyst, at a temperature in a range of 200° C. to 600° C. and at a pressure in a range of 0.5 $kg/cm^2$ to 10 $kg/cm^2$, to produce a second stream comprising olefins, $H_2O$, methane, ethane, and propane, wherein said at least one second catalyst is ZSM-5;

(e) separating $H_2O$, methane, ethane and propane from said second stream to obtain said olefins; and (f) recycling the separated $H_2O$, methane, ethane and propane to step (a) for producing said syngas.

2. The process as claimed in claim 1, wherein said olefins is at least one of ethylene and propylene.

3. The process as claimed in claim 1, wherein the separated portion of $CO_2$ in step (c) and the separated $H_2O$ in step (e) are recycled to step (a), for producing said syngas by reforming at least one of:

natural gas; and one of the separated methane, ethane, and propane, with $CO_2$.

* * * * *